(12) United States Patent
Pierre et al.

(10) Patent No.: US 8,308,785 B2
(45) Date of Patent: Nov. 13, 2012

(54) MULTI-ACCESS BLANKET

(75) Inventors: Joseph Pierre, Libertyville, IL (US);
Rachel Starr, Randolph, MA (US);
Alan Stec, East Bridgewater, MA (US)

(73) Assignee: Smiths Medical ASD, Inc., Rockland, MA (US)

( * ) Notice: Subject to any disclaimer, the term of this patent is extended or adjusted under 35 U.S.C. 154(b) by 940 days.

(21) Appl. No.: 12/379,259

(22) Filed: Feb. 18, 2009

(65) Prior Publication Data
US 2010/0211141 A1 Aug. 19, 2010

(51) Int. Cl.
*A61F 7/00* (2006.01)
(52) U.S. Cl. ........................................ 607/104; 607/107
(58) Field of Classification Search ............ 607/96, 607/104–114; 604/113, 114; 34/96–99; 5/421, 423
See application file for complete search history.

(56) References Cited

U.S. PATENT DOCUMENTS

| | | | |
|---|---|---|---|
| 5,545,194 A * | 8/1996 | Augustine | 607/104 |
| 5,735,890 A | 4/1998 | Kappel et al. | |
| 5,773,275 A | 6/1998 | Anderson et al. | |
| 5,839,133 A | 11/1998 | Dickerhoff et al. | |
| 5,928,274 A * | 7/1999 | Augustine | 607/107 |
| 2006/0178717 A1* | 8/2006 | Harris et al. | 607/114 |
| 2008/0027522 A1 | 1/2008 | Bieberich | |
| 2009/0248120 A1 | 10/2009 | Starr et al. | |

OTHER PUBLICATIONS

PCT International Search Report and Written Opinion, ISA/KR, Oct. 7, 2010.

* cited by examiner

*Primary Examiner* — Matthew F Desanto
(74) *Attorney, Agent, or Firm* — Louis Woo

(57) ABSTRACT

A convective warming blanket has a head portion and a plurality of peripheral sections extending orthogonally from each side of a central section that extends uninterrupted from a proximal end below the head portion to a distal foot end of the blanket. Each peripheral section is separable from its adjacent peripheral section by a frangible or tearable common seal. At least one through passage connects each peripheral section to the central section, so that the peripheral sections are inflated when heated air is input to the blanket. The multiple peripheral sections each are movable relative to the central section, so that different body parts of the patient may be selectively accessed. The head portion of the blanket is formed by two tubular sections that extend from the proximal portion of the blanket to encircle the head of the patient, when the blanket is placed over the patient.

19 Claims, 3 Drawing Sheets

MULTI-ACCESS BLANKET

FIELD OF THE INVENTION

The present invention relates to convective warming blankets, and more particularly relates to a blanket that is designed to allow a clinician or surgeon to selectively gain access to different areas of the body of the patient covered by the blanket.

BACKGROUND OF THE INVENTION

The use of inflatable convective blankets for pre-operative, post-operative and/or intra-operative warming of a patient in surgery or to prevent the patient from hypothermia is known. During surgery, there is often a need for the surgeon or clinician to gain access to a given part of the body of the patient. Previously, multiple warming blankets may be used to ensure that a given body part of the patient is exposed, while other body parts of the patient are covered to maintain warmth to the patient. However, the use of multiple blankets often is cumbersome. Moreover, there are instances where after a given body part of the patient has been accessed, other body parts of the patient may have to be accessed, with the previously accessed body part(s) of the patient having to be kept warm. There is currently a multi-access blanket in the market sold by Arizant under product number Model 315. That blanket covers only the body of the patient.

SUMMARY OF THE PRESENT INVENTION

The convective blanket of the present invention is a full body inflatable warming blanket that has a main body having a central section that extends from a proximal portion of the blanket to the foot or distal end of the blanket. The proximal portion of the blanket has a proximal end that is below the head of the patient. A head portion is connected to and in fluid communication with the proximal portion. Extending orthogonally to either side of the central section are a plurality of peripheral sections each foldable relative to the central section for selectively exposing a body part or portion of the patient along the length of the blanket. Adjacent peripheral sections are connected by a frangible or tearable common seal that allows the peripheral sections to be separated and movable relative to the rest of the blanket, for example by being folded toward the central section of the blanket to selectively expose the body part of the patient covered by that particular peripheral section. The frangible or tearable common seal that separates adjacent peripheral sections may already be cut along its length or may have a series of slits along its length that allows the adjacent peripheral sections to readily separate from each other when a tearing force is applied to the common seal.

The head portion is formed by two tubular sections that extend from the proximal portion. The tubular sections each have a closed end that meets, or removably attached to each other by means of a common seal that may already have been separated or have a tearable slit therealong. The tubular sections together form an enclosure for the head of a patient, when the blanket is placed over the patient. Apertures are provided at the tubular sections to direct heated air inputted to the blanket to the head of the patient. A plastic cover sheet or flap has an edge or a portion thereof attached to the proximal portion of the blanket, and is foldable over the head portion for covering the head of the patient to maintain the warm air under the cover.

The blanket of the present invention is made from two air impermeable layers or sheets selectively bonded at different locations for forming an inflatable blanket structure with the various central and peripheral sections. The sheet or layer that comes into contact with the patient has punched therealong apertures at the various sections so that heated air input into the blanket for inflating the same is output from the apertures to warm the patient. Multiple air inlets may be provided at the proximal portion of the blanket, with only one of the air inlets being used for inputting the heated air into the blanket.

To facilitate the flow of heated air within the blanket, there is provided at the central section of the blanket a central seal that extends from the proximal portion of the blanket though the middle portion to approximately the beginning of the distal portion of the blanket. A second central seal in longitudinal alignment with the first central seal extends along the distal portion of the blanket so that two through channels are provided along the central section of the blanket for guiding the heated air from the proximal portion of the blanket to the distal portion of the blanket.

The peripheral sections that extend orthogonally from the respective sides of the central section each are in fluid communication with the central section by at least one through passage, so that each of the peripheral sections at either side of the central section is in fluid communication with the central section and is inflated when temperature treated air such as heated air is input to the blanket.

The present invention therefore relates to an inflatable convective blanket for selectively exposing different parts or portions of the body of a patient covered thereby that comprises a main body having a proximal portion that extends from a proximal end below the head of a patient, a distal portion at the foot or distal end of the blanket and a middle portion sandwiched between the proximal and distal portions, and a head portion connected to the proximal portion. The main body of the blanket further comprises a central section that extends longitudinally uninterrupted from the proximal end to the distal end of the blanket, a plurality of peripheral sections that extend orthogonally from the central section, each of the peripheral sections movable at least relative to the central section to expose a particular part of the body of the patient. The central section and the peripheral sections are fluidly interconnected so that the head portion, the central section and the peripheral sections are inflatable by temperature treated air input into the blanket at for example the proximal portion. Each of the central section and peripheral sections has apertures at the surface that contacts the patient for outputting the temperature treated air to the patient.

The present invention is also directed to a convective blanket for selectively exposing different parts of the body of a patient that comprises a main body having a proximal portion, a distal portion, a middle portion sandwiched between the proximal and distal portions, and a central section that extends longitudinally uninterrupted from the proximal end to the distal end of the blanket, and a head portion connected to and in fluid communication with the proximal portion. There are first two peripheral sections each extending orthogonally from a corresponding side of the central section at proximately the middle portion of the blanket, and second two peripheral sections each extending orthogonally from a corresponding side of the central section at approximately the distal portion of the blanket. The first and second peripheral sections on each side of the central section being adjacent to each other and each of the peripheral sections is fluidly connected to the central section so that the central and peripheral sections are inflatable by temperature treated air input to the blanket, as is the head portion. Each of the peripheral sections is movable relative to the rest of the blanket to expose a corresponding part of the body of the patient, the central and the peripheral sections each having apertures at the surface that contacts the patient for outputting the temperature treated air to the patient.

The present invention is further related to a full body convective warming blanket with a head portion that enables selective accessing of multiple parts of the body of the patient. The blanket is formed by two air impermeable sheets sealingly bonded at different locations. The blanket comprises a main body having a proximal portion, a distal portion and a middle portion sandwiched between the proximal and distal portions, and a head portion connected to and in fluid communication with the proximal portion. The main body further includes a central section that extends longitudinally uninterrupted along the proximal, middle and distal portions, a first plurality of peripheral sections each extending orthogonally from one side of the central section and a second plurality of peripheral sections each extending orthogonally from the other side of the central section. Respective adjacent pairs of the first and second plurality of sections are removably connected by a tearable common seal. The first and second plurality of peripheral sections each are fluidly connected to the central section so that all sections of the blankets are inflated by temperature treated air input to the blanket. Each of the first and second plurality of peripheral sections is movable relative to the rest of the blanket to selectively expose at least a particular body portion of the patient, and apertures are provided at the sheet in contact with the patient for outputting the temperature treated air to the patient.

BRIEF DESCRIPTION OF THE FIGURES

The present invention will become apparent and the invention itself will be best understood by reference to the following description of the invention taken in conjunction with the following drawings, wherein.

DETAILED DESCRIPTION OF THE INVENTION

Figure 1:
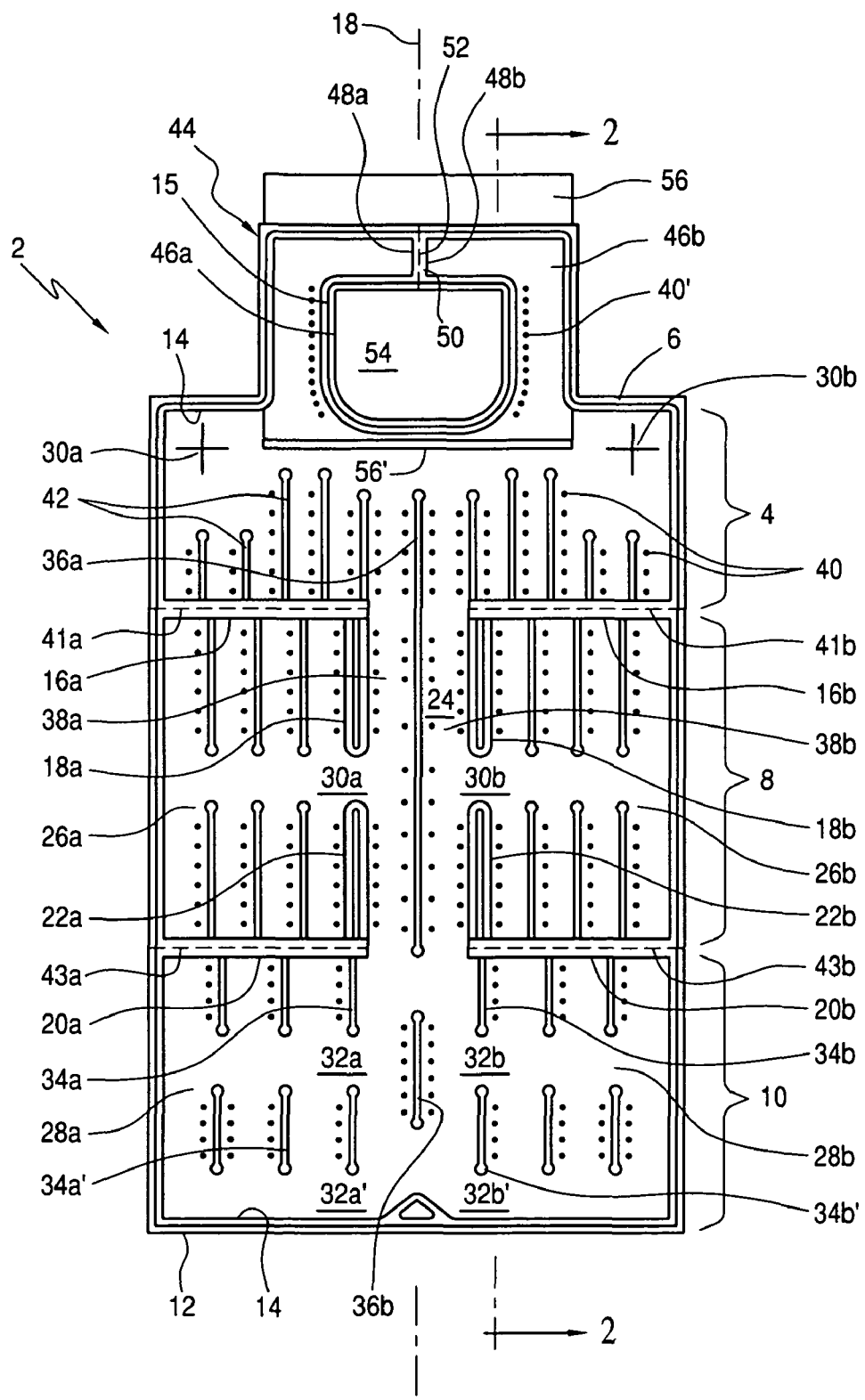
FIG. 1 is a plan view of the convective warming blanket of the instant invention showing both the upper and lower layers of the blanket.

With reference to FIG. 1, blanket 2 of the instant invention is shown to have a proximal portion 4 that extends from a proximal end 6 to the beginning of a middle portion 8, which in turn extends to the beginning of a distal portion 10 that ends at a distal end 12 of the blanket. Proximal portion 4, middle portion 8 and distal portion 10 in combination may be referred to as the main body of blanket 2. Blanket 2 is made of two air impermeable sheets or layers as is conventionally known. In FIG. 1, for illustration purposes, the sheets are shown together with the upper sheet superposed over the lower sheet so that the lower sheet, or the bottom layer of the blanket with the myriad apertures, can also be seen. The two sheets are sealingly bonded at various locations of the blanket to form an inflatable structure as is also conventionally known. For example, the periphery of the blanket is bonded by an outer periphery seal 12 and an inner periphery seal 14. The enclosure formed by the tubular sections of the head portion of the blanket, to be discussed in more detail below, is defined by an internal periphery seal 15.

In addition to the periphery seals 12 and 14, a first set of seals 16a and 16b are formed orthogonal to the longitudinal axis 18 of blanket 2. Seals 16a and 16b each extend from periphery seal 14 towards the center of the blanket until meeting with longitudinal seals 18a and 18b, respectively. For the exemplar blanket, the first set of seals 16a and 16b may be located approximately at the junction where proximal portion 4 meets middle portion 8, and the second set of seals 20a and 20b extend orthogonally from peripheral seal 14 inwards toward the blanket at approximately the junction where proximal portion 8 meets distal portion 10. Orthogonal seals 16a and 16b join with longitudinal seals 18a and 18b, respectively, while orthogonal seals 20a and 20b join with longitudinal seals 22a and 22b, respectively. The area of the blanket that extends longitudinally uninterrupted from proximal end 6 to distal end 12 between longitudinal seals 18a, 18b and 22a, 22b may be referred to as the central section of the blanket, and is designated 24 in FIG. 1. For the exemplar blanket embodiment of FIG. 1, orthogonal seals 16a, 16b and 20a, 20b may also be referred to as the horizontal seals, while seals 18a, 18b and 22a, 22b may also be referred to as the vertical seals.

With the partition of blanket 2 by horizontal seals 16a, 16b and 20a, 20b and vertical seals 18a, 18b and 22a, 22b, the portions of the blanket that are partitioned by those seals may be considered peripheral sections that extend orthogonally from central section 24. Thus, peripheral section 26a is bonded by seals 16a, 18a, 22a and 20a; while peripheral section 26b is bonded by seal 16b, 18b, 22b and 20b. Each of peripheral sections 26a and 26b extend from central section 24 at approximately the middle portion 8 of blanket 2. Similarly, peripheral sections 28a and 28b, partitioned by horizontal seals 20a and 20b, respectively, each extend from central section 24 at approximately the distal portion 10 of blanket 2.

To inflate the blanket, multiple air inlets 30a and 30b are provided proximate to proximal end 6 of proximal portion 4. Only one of those air inlets 30a, 30b is used when in operation. To inflate blanket 2, a hose of an air warmer, not shown, is mated to one of the air inlets, and temperature treated air, such as for example heated air, is input to blanket 2 to inflate the blanket structure.

So that the various portions and sections of the blanket 2 are inflated by the temperature treated air input to the blanket, there is at least one through passage interconnecting each of the various peripheral sections of the blanket to central section 24 so that fluid communication paths are established among the peripheral sections and the central section 24. As shown, peripheral section 26a is fluidly interconnected to central section by through passage 30a defined between the two opposed ends of vertical seals 18a and 22a. A corresponding through passage 30b establishing fluid communication between peripheral section 26b and central section 24 is defined between the two opposed ends of vertical seals 18b and 22b. For peripheral section 28a, there are two through passages 32a and 32a' respectively defined between the opposed ends of internal seals 34a and 34a' that extend longitudinally in distal portion 10 and between the other end of seal 34a' and distal end 14 of blanket 2. Similarly, two through passages 32b and 32b' are respectively defined by the opposed ends of internal seals 34b and 34b' that extend longitudinally in proximal portion 10 and the other end of seal 34b' and distal end 14 of blanket 2. Thus, the various peripheral sections 26a, 26b and 28a, 28b each are in fluid communication with central section 24, and are therefore fluidly interconnected in blanket 2.

To facilitate the flow of air in blanket 2, a central seal 36a extends in blanket 2 from proximal portion 4 through middle portion 8 to approximately the junction where middle portion 8 meets distal portion 10. A second central seal 36b in alignment with but separated from central seal 36a extends longitudinally along distal portion 10. With the longitudinal seals 36a and 36b, two channels 38a and 38b are formed along central section 24, so that the heated air input from the air inlet, for example 30b, at proximal portion 4 is guided by those air channels 38a and 38b to peripheral sections 26a, 26b, 28a and 28b by means of the different though passages 30a, 30b, 32a and 32a' and 32b and 32b'. Proximal portion 4 is also inflated by the input air.

To enhance inflation and the output of the heated air to the patient which are done by means of the apertures 40, a number of seals 42 are provided in blanket 2. The respective configurations of seals 42 and the apertures 40 adjacent thereto are illustrated in FIG. 1. Common seals 16a and 16b that extend orthogonally from central section 24 and which provide a demarcation separating proximal portion 4 from middle portion 8 have corresponding slits 41a and 41b formed thereallong, so that section 26a and 26b each may be separated from proximal portion 4 of the blanket, when a tearing force is applied to those common seals. Similarly, slits 43a and 43b are formed along common seals 20a and 20b which separate peripheral sections 26a and 26b from peripheral sections 28a and 28b, respectively. Thus, sections 26a and 26b each may be separated from the rest of the blanket, and are foldable away from the rest of the blanket to selectively expose particular body portions or parts of the patient being covered by blanket 2. As should be apparent, section 26a may be folded or moved to along seals 18a and 22a while section 26b may be moved or folded longitudinally along seals 18b and 22b. Likewise, section 28a may be folded or moved relative to central section 24, or the rest of the blanket by first tearing along slit 43a and then folding along seals 34a and 34a'; while section 28b may be folded along longitudinal seals 34b and 34b', after section 28b has been separated from section 26b by tearing along slit 43b.

Instead of a slit, frangible common seals 16a and 16b, 20a and 20b may be made with tearable material along their centerline or mid-section so that the integrity of those common seals would remain intact for bonding the upper and lower sheets of the blanket structure to define the peripheral sections that extend orthogonally from the longitudinal central section 24. As discussed previously, the lower sheet or layer of the blanket that comes into contact with the patient is punched with myriad apertures 40 that output the heated air to the different body parts of the patient by way of the different sections or portions of the blanket.

Blanket 2 also has a head portion 44 that is defined by two tubular sections 46a and 46b that extend from proximal portion 4. Tubular sections 46a and 46b are joined at their respective closed ends 48a and 48b by a common seal 50 that has a series of slits 52 that allow the tubular sections 46a and 46b to be separated. Alternatively, the closed ends 48a and 48b may not be attached or joined at all prior to use so long as they are positioned opposed to each other as shown in FIG. 1 to effect the enclosure 54 for the head of the patient when fully inflated. As configured, tubular sections 46a and 46b form an enclosure 54 that encircles and exposes the head of the patient, when the patient is covered by blanket 2. Apertures 40' are provided at each of the tubular sections 46a and 46b for outputting the heated air towards the head of the patient. To prevent the heated air from readily escaping to the environment, a clear flap 56 that may be made of plastic has a portion or edge 56' attached to proximal portion 4, so that flap 56 may be folded over enclosure 54 to maintain the heat directed to the head of the patient under the flap.

Figure 2:
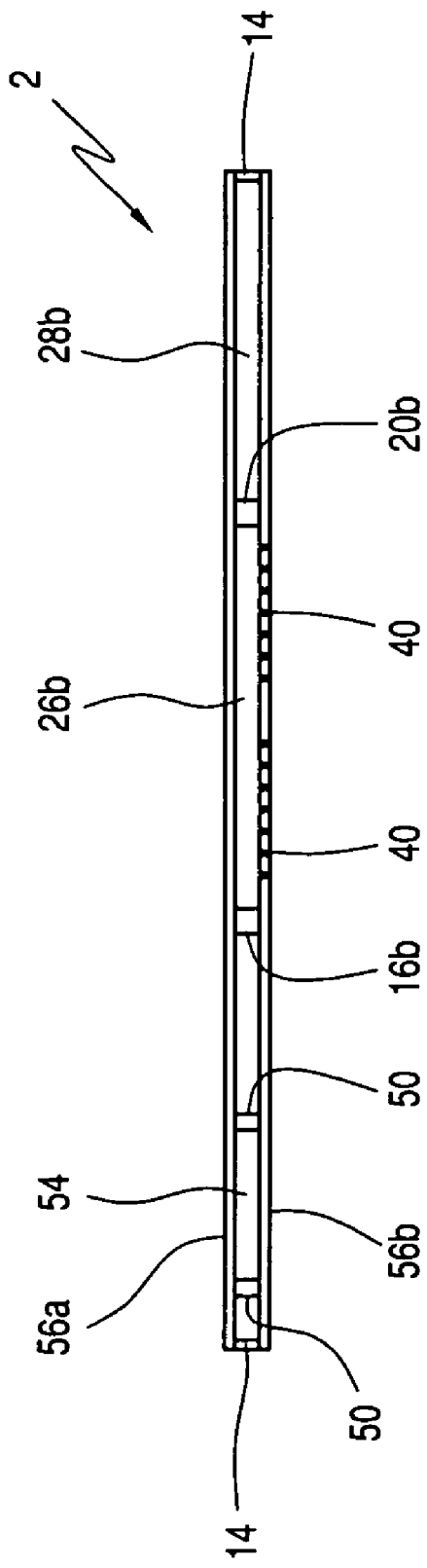
FIG. 2 is a cross-sectional view along section 2-2 of the FIG. 1 blanket.

FIG. 2 is a sectional view of blanket 2 along cross-section 2-2 of FIG. 1 that shows a first layer or sheet 56a bonded to a lower layer or sheet 56b by means of periphery seal 14 and other bonding seals such as 16a and 20b. FIG. 2 shows peripheral section 26b and the apertures 40 along section 2-2 that output the heated air from peripheral section 26b to the patient covered by blanket 2. FIG. 2 further shows enclosure 54 defined by the tubular sections 46a and 46b for head portion 44. For simplicity of illustration, FIG. 2 is not drawn to scale, and the various sections and portions are not shown as being inflated.

Figure 3:
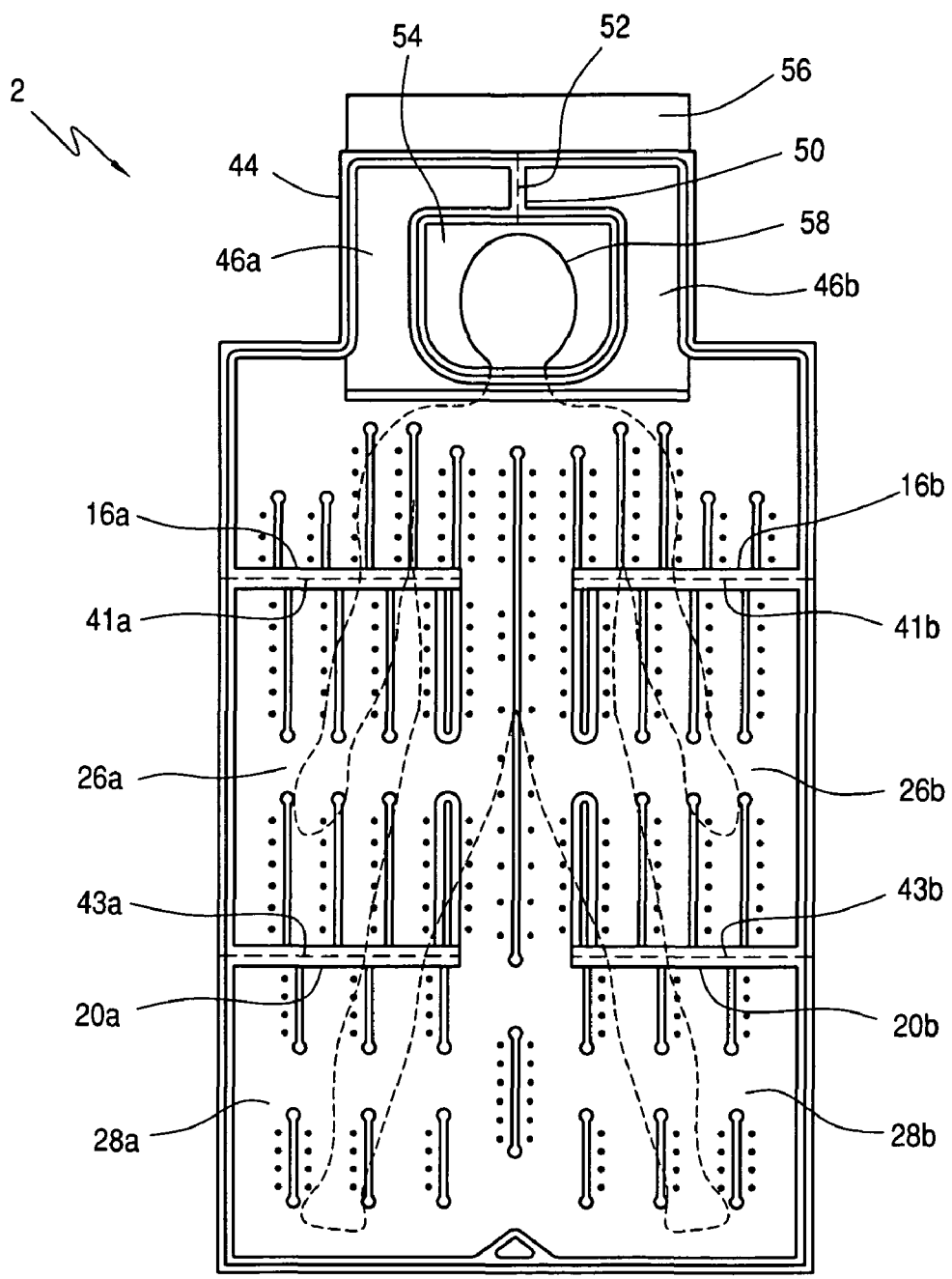
FIG. 3 shows the placement of the blanket of the instant invention over a patient.

FIG. 3 shows blanket 2 covering a patient 58. As shown, the head of the patient 58 is positioned in enclosure 54 of head portion 44. For the FIG. 3 illustration, the head of the patient is covered by the clear plastic flap 56. The different parts or portions of the body of the patient may be accessed by the moving and folding back of the different peripheral sections relative to the rest of blanket 2. For example, to gain access to the right hand and right thigh of the patient, peripheral section 26a may be separated along common seals 16a and 20a, via tearable slits 43a and 41a, from the rest of the blanket, and then folded along vertical seals 18a and 22a over central section 24. Similarly, section 26b may be separated along common seals 16b and 20b and folded relative to central section 24 to expose the left thigh of the patient. Sections 28a and 28b each likewise may be folded toward the central section 24 to expose the right and left legs, respectively, of the patient. So, too, both peripheral sections 28a and 28b may be folded along horizontal common seals 20a and 20b toward the proximal end of the blanket to expose both legs of the patient. In the same vein, peripheral sections 26b and 28b may both be folded over central section 24 to expose the left side of the patient, while peripheral sections 26a and 28a may both be folded over central section 24 to expose the right side of the patient. As should be apparent, the different peripheral sections may be folded in various combinations to selectively access different parts or portions of the body of the patient, while at the same time maintaining warmth for the rest of the patient.

Although the present invention blanket is discussed with reference to a proximal portion, a middle portion, a distal portion, and two adjacent peripheral sections at each longitudinal side of the blanket, additional smaller dimensioned peripheral sections may extend from each side of central section 24 to enable a more selective accessing of the different body parts or portions of the patient. For example and without limitation, there may be four peripheral sections extending from each side of central section 24, with the adjacent peripheral sections separated by a common tearable seal and longitudinal seals that define how far those peripheral sections may be folded or moved relative to the rest of the blanket. The vertical or longitudinal seals that define how far the peripheral sections may be folded over the central section do not need to be in alignment along the length of the blanket, as the lengths of the horizontal common seals may vary and the width of the central section does not have to remain constant along the entire length of the blanket, so that for example a first peripheral section may be folded back to expose one eighth of the width of the blanket whereas another peripheral section may be folded back to expose one fourth of the width of the blanket. The only thing that is required is that each of the peripheral sections be fluidly interconnected to the central section or some common portion of the blanket where the input air flows so that all the peripheral sections are inflated when the temperature treated air is input into the blanket.

The invention disclosed above is subject to many variations, modifications and changes in detail. Thus, it is intended that all matters described throughout this specification and shown in the accompanying drawings be interpreted as illustrative only and not in a limiting sense. Accordingly, it is intended the invention be limited only by the spirit and scope of the hereto appended claims.

The invention claimed is:

1. An inflatable convective blanket for selectively exposing different parts of the body of a patient covered thereby comprising: a main body including a proximal portion that extends from a proximal end below the head of the patient, a distal portion that extends to a distal end of the blanket and a middle portion sandwiched between the proximal and distal portions, and a head portion connected to the proximal portion for the head of the patient, the main body further having a central section that extends longitudinally uninterrupted from the proximal end to the distal end, a plurality of peripheral sections extending orthogonally from the central section, the head portion, the central section and the peripheral sections are fluidly interconnected and are inflated by temperature treated air input into the blanket, the patient being covered by at least the inflated central and peripheral sections of the inflated blanket, adjacent peripheral sections being separated by a common tearable seal, wherein each of the inflated peripheral sections from at least the middle portion to the distal portion is separable from its adjacent peripheral section along the common tearable seal and foldable relative to the central section to expose a particular part of the body of the patient, each of the central section and peripheral sections has apertures at its surface that contacts the patient for outputting the temperature treated air to the patient.

2. Blanket of claim 1, wherein the head portion comprises two tubular sections each extending from and fluidly connected to the proximal portion so that each tubular section is inflated when the central section and peripheral sections of the blanket are inflated, the tubular sections having respective closed ends that meet or are removably attached to form an inflatable enclosure for the head of the patient.

3. Blanket of claim 2, wherein the tubular sections each have apertures thereat for outputting the temperature treated air to the head of the patient.

4. Blanket of claim 2, further comprising a clear plastic flap having one edge attached to the proximal portion and foldable over the head portion to cover the head of the patient encircled the tubular enclosure.

5. Blanket of claim 1, wherein respective ones of the peripheral sections extend orthogonally from each side of the central section at the middle portion and respective other ones of the peripheral sections extend orthogonally from each side of the central section at the distal portion.

6. Blanket of claim 5, wherein the peripheral sections extending orthogonally from the respective sides of the central section each are removably attached to its adjacent peripheral section by a first common tearable seal, a second common tearable seal running parallel to the first tearable common seal removably joining the peripheral sections extending orthogonally from the respective sides of the central section at the middle portion to the proximal portion of the blanket.

7. Blanket of claim 1, wherein there are two peripheral sections at each side of the central section, each of the peripheral sections is in fluid communication with the central section by at least one through passage at its center, the two peripheral sections at each side of the central section being separable from each other and movable relative to each other and the central section so that either or both peripheral sections are movable relative to the central section to expose respective parts of the body of the patient.

8. Blanket of claim 1, wherein the central section comprises two longitudinal channels wherethrough the temperature treated air flows, the two channels separated by a first longitudinal central seal that extends a predetermined distance away from the proximal end to approximately a common orthogonal axis of the blanket where respective orthogonal seals separate the respective pairs of adjacent peripheral sections extending orthogonally from the sides of the central section, a second central seal extending along the distal portion of the blanket longitudinally in alignment with but separate from the first central seal.

9. Blanket of claim 1, further comprising at least one air inlet at the proximal portion of the blanket whereat the temperature heated air is input to the blanket.

10. Blanket of claim 1, wherein the blanket is made of two air impermeable layers selectively bonded at different locations to sealingly form the fluidly interconnected portions and sections, the layer in contact with the patient having apertures selectively punched therealong for outputting the temperature treated air to the patient when the patient is covered by the blanket and the blanket is inflated to its working condition by the temperature treated air.

11. A convective blanket for selectively exposing different parts of the body of a patient covered by the blanket comprising: a main body including a proximal portion that extends from a proximal end below the head of the patient, a distal portion that extends to a distal end of the blanket and a middle portion sandwiched between the proximal and distal portions, and a head portion connected to the proximal portion for the head of the patient, the main body further having a central section that extends longitudinally uninterrupted from the proximal end to the distal end and in fluid communication with the proximal, central and distal portions, first at least two peripheral sections each extending orthogonally from a corresponding side of the central section at approximately the middle portion, second at least two peripheral sections each extending orthogonally from a corresponding side of the central section at approximately the distal portion, the first and second peripheral sections at each side of the central section being adjacent to each other and separated by a frangible common seal, wherein the head portion is in fluid communication with the proximal portion and each of the peripheral sections is fluidly connected to the central section so that the head portion, the central section and the peripheral sections are inflatable by temperature treated air input into the blanket, the patient being covered by the inflated central and peripheral sections of the inflated blanket, each of the peripheral sections separable from its adjacent peripheral section along their frangible common seal to be foldable relative to the rest of the blanket to expose a corresponding part of the body of the patient, the central section and the peripheral sections each having apertures at the surface that contacts the patient for outputting the temperature treated air to the patient.

12. Blanket of claim 11, wherein the head portion comprises two tubular sections each extending from and fluidly connected to the proximal portion so that each tubular section is inflated when the blanket is inflated by the temperature treated air, the tubular sections having respective closed ends that meet or are removably attached to form an enclosure to surround the head of the patient, wherein the tubular sections each have apertures thereat for outputting the temperature treated air to the head of the patient.

13. Blanket of claim 12, further comprising a clear plastic flap having one edge attached to the proximal portion and foldable over the head portion to cover the head of the patient surrounded by the tubular enclosure.

14. Blanket of claim 11, wherein the central section comprises two longitudinal channels wherethrough the temperature treated air flows, the two channels separated by a first longitudinal central seal that extends from the proximal portion to approximately where the middle and distal portions meet, a second central seal extending along the distal portion of the blanket longitudinally in alignment with but separate from the first central seal.

15. Blanket of claim 11, further comprising at least one air inlet at the proximal portion of the blanket whereat the temperature heated air is input to the blanket.

16. Blanket of claim 11, wherein the blanket is made of two air impermeable layers selectively bonded at different locations to sealingly form the fluidly interconnected portions and sections, the layer in contact with the patient having apertures selectively punched therealong for outputting the temperature treated air to the patient when the patient is covered by the blanket and the blanket is inflated to its working condition by the temperature treated air.

17. A full body convective warming blanket that enables selective accessing of multiple parts of the body of a patient covered thereby formed by two air impermeable sheets sealingly bonded at different locations, comprising: a main body including a proximal portion that extends from a proximal end below the head of the patient, a distal portion that extends to a distal end of the blanket and a middle portion sandwiched between the proximal and distal portions, and a head portion connected to and in fluid communication with the proximal portion for the head of the patient, the main body further including a central section extending longitudinally uninterrupted along the proximal, middle and distal portions from the proximal end to the distal end, first plurality of peripheral sections each extending orthogonally from one side of the central section, second plurality of peripheral sections each extending orthogonally from other side of the central section, each respective adjacent pairs of the first and second plurality of peripheral sections removably connected by a tearable common seal, each of the respective first and second plurality of peripheral sections fluidly connected to the central section so that the head portion and all sections at the main body of the blanket are inflated by temperature treated air input into the blanket, the patient being covered by the inflated central and peripheral sections of the inflated blanket, each of the first and second plurality of inflated peripheral sections foldable relative to at least the central section of the blanket to selectively expose at least a particular body part of the patient, apertures provided at the sheet in contact with the patient for outputting the temperature treated air to the patient.

18. Blanket of claim 17, wherein the head portion comprises two tubular sections each extending from and fluidly connected to the proximal portion so that each tubular section is inflated when the blanket is inflated by the temperature treated air, the tubular sections having respective closed ends that meet or are removably attached to form an enclosure that surrounds the head of the patient, wherein the tubular sections each have apertures thereat for outputting the temperature treated air to the head of the patient.

19. Blanket of claim 17, further comprising a clear plastic flap attached to the proximal portion and foldable over the head portion to cover the head of the patient surrounded by the tubular enclosure.

* * * * *